United States Patent [19]

Rapp et al.

[11] 4,060,388

[45] Nov. 29, 1977

[54] SPECIMEN HOLDING DEVICE AND METHOD OF USING SAME

[75] Inventors: Wolfgang Rapp, Edingen; Karl-Heinz Haas, Wetzlar; Heribert Luessem, Braunfels, all of Germany

[73] Assignee: Ernst Leitz GmbH Wetzlar, Wetzlar, Germany

[21] Appl. No.: 674,122

[22] Filed: Apr. 6, 1976

[30] Foreign Application Priority Data

Apr. 9, 1975 Germany ........................ 7511053[U]

[51] Int. Cl.$^2$ ........................ G01L 3/00; G01N 21/00; G01N 31/02; G01N 33/16

[52] U.S. Cl. ................................ 23/230 R; 23/230 B; 23/253 R; 23/259; 23/292; 356/246

[58] Field of Search ...................... 23/253 R, 259, 292, 23/230 B, 230 R; 356/246; 195/127

[56] References Cited

U.S. PATENT DOCUMENTS

| | | | |
|---|---|---|---|
| 3,378,347 | 4/1968 | Saravis | 23/253 R |
| 3,378,481 | 4/1968 | Saravis et al. | 23/253 R X |
| 3,389,966 | 6/1968 | Saravis | 23/253 R X |
| 3,404,780 | 10/1968 | Jungner | 23/253 R |
| 3,489,521 | 1/1970 | Buckle et al. | 23/253 R |
| 3,713,771 | 1/1973 | Taylor et al. | 23/253 R X |
| 3,718,439 | 2/1973 | Rosse et al. | 23/253 R X |
| 3,913,790 | 10/1975 | Seidel | 23/253 R X |

*Primary Examiner*—Joseph Scovronek
*Attorney, Agent, or Firm*—Bacon & Thomas

[57] ABSTRACT

Disclosed is a specimen holding device suitable for holding fluid substances which are to be analyzed and which cause clouding or color change by reacting with a reagent, comprising a generally solid piece of transparent material containing a plurality of elongated recesses having the longitudinal axis thereof extending into the material, preferably perpendicularly to the top surface of a soiid piece. Preferably, the recesses are iterconnectedat their lower ends with a filling channel which terminates on one side surface of the device. Also disclosed is a method for using the device.

25 Claims, 5 Drawing Figures

SPECIMEN HOLDING DEVICE AND METHOD OF USING SAME

BACKGROUND OF THE INVENTION

A considerable number of proteins in the blood and in the body can be quantitatively determined today with immunological processes which utilize special animal serums. Although these determintion methods at the present time are applied only on a case-by-case basis in connection with certain pathological conditions and only with regard to from 3 to 5 proteins, respectively, they have produced an enrichment in diagnostic techniques, in the prevention and in the therapeutic treatment of disease. These investigations are carried out in the following manner.

Located on a transparent plate is a gel layer of from 1 to 2 mm in thickness containing the specific antiserum. Reservoirs having a diameter of from 1 to 2 mm are stamped into the gel layer for reception of from 5 to 10 microliters of the sample. Radial precipitates are produced as a function of the concentration of the proteins to be measured, and the areas of the precipitates are proportional to the concentration of the proteins. By means of calibrated standard samples, the concentration of the substance to be determined is calculated using a regression function. The maximum diameter of the precipitates lies between 0.5 and 1.5 cm.

The disadvantages of this process reside in the fact that an evaluation is possible only after completion of the reaction (2 to 5 days). A further disadvantage is that differing results and differing variation coefficients are obtained depending upon the mathematical evaluation employed.

Furthermore, pipetting errors also influence the measurement results, because this result is directly dependent upon the volume of the substance employed. Moreover, it cannot always be assured that the precipitate has an exact circular configuration, which renders necessary a measurement of longitudinal distortion in at least two directions. The thickness of the reagent layer also influences the measured results.

It is also known to carry out reaction determinations of this type with the aid of individual, transparent glass tubes, in which the fluids to be reacted with one another are placed. This method produces more exact measurement results, since the result is nearly independent of the volume and since this method leads to quicker measurements. Disadvantageous in connection with this procedure is, however, that the tubes must be individually prepared.

SUMMARY OF THE INVENTION

It is therefore an object of the present invention to provide an improved specimen holding device for use in a measurement procedure of the last-mentioned type and an improved method of using same.

It is a further object of the invention to provide an improved specimen holding device which enables the determination procedure to be carried out economically.

A further object of the invention resides in the provision of an improved specimen holding device which is readily suitable for automatic application in carrying out the determination procedure.

It is also an object of the invention to provide an improved specimen holding device which avoids the disadvantages attendant the known types of devices.

In accomplishing the foregoing objects, there has been provided in accordance with the present invention a specimen holding device suitable for holding fluid substances which are to be analyzed and which cause clouding or color change by reacting with a reagent which is contained in the device and in which the substances are placed, the device comprising a generally solid piece of a transparent material, preferably in the form of a rectangular block or of an arcuate section, containing a plurality of elongated recesses, preferably of generally circular cross-section, having the longitudinal axis thereof extending into the piece of material, preferably perpendicularly to the top surface thereof. These recesses are adapted for receiving the reagent and subsequently for additionally receiving the substance to be analyzed. According to the invention, the recesses may be in the form of either dead-end bores, or in the form of bores passing entirely through the piece of material. In the latter instance, closure means are provided for closing off the lower ends of the bores.

In accordance with one embodiment of the invention, the device further comprises canal means within the solid piece for interconnecting the lower ends of the recesses, and these canal means exit from at least one surface of the solid piece, preferably from one of the side surfaces thereof. This feature is utilizable irrespective of whether the recesses are dead-end bores or whether they pass completely through the device and are subsequently closed off with a closure means.

In accordance with another embodiment of the device, the recesses are shaped in such a manner as to have at least one minor sidewall surface, preferably a plurality of such planar sidewall surfaces, wherein one of these surfaces forms an angle different from 90° with the longitudinal axis of the solid body.

According to yet another feature of the present invention, at least one of the longitudinal side surfaces of the solid body is divided up into a plurality of steplike segments, each segment having a wall surface arranged at a common acute angle with respect to the longitudinal axis of the solid body.

Other features, objects and advantages of the invention will become apparent from the following detailed description of preferred embodiments, considered together with the figures of drawing attached hereto.

DETAILED DESCRIPTION OF THE INVENTION

The subject matter of the invention is a specimen holding device of the type referred to in the introductory portion of the application, which device is characterized in that the device is produced from a transparent material and comprises a plurality of elongated recesses extending with their longitudinal axis into the material. The recesses serve for accepting the reagent and subsequently for additionally accepting the substance to be investigated. In addition, a recess can be provided for receiving an identifying indicia, for example, a data-bearing element. The specimen holding device preferably has a rectangular cross-section and the recesses preferably extend with their longitudinal axis perpendicular to the top surface of the device. The device can be designed also with a ring-shaped configuration or as a partial segment of such a ring. The recesses provided for the reagent may preferably have a circular cross section, and they may be designed as dead-end bores. By means of an interconnecting canal, preferably one which exits at one side of the device, the lower ends of the recesses can be interconnected with one another. Alternatively, the recesses for the reagent can be designed to pass completely through the device. Advantageously, the specimen carrying device comprises on one of its exterior surfaces at least one gear-tooth system for transporting the device, or alternatively, this transport system can be incorporated into a closure device for closing-off the recesses in the design where they pass entirely through the device. The recesses can also be comprised of planar side surfaces wherein at least one of the side surfaces is arranged so that it forms an angle other than 90° with the longitudinal axis of the device. According to this last-mentioned design feature, it is also advantageous to subdivide one side surface of the device into a plurality of segments, with each segment having a surface arranged at the same angle with respect to the longitudinal axis of the device. Finally, the novel specimen holding device of the invention can comprise on at least one of its outer surfaces at least one projection and/or at least one recess for coupling the device with another like device.

Figure 1:
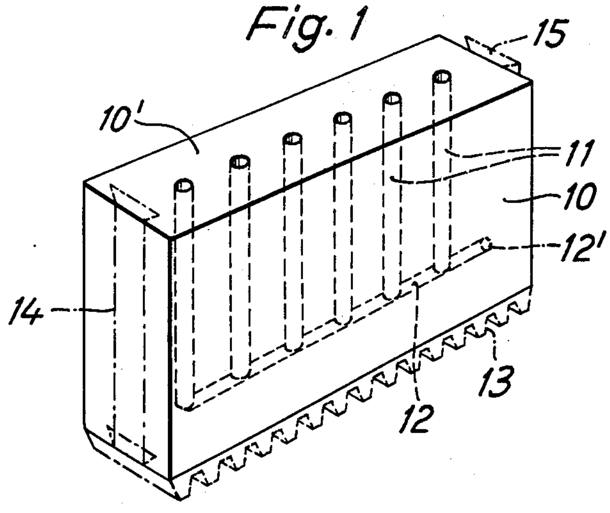
FIG. 1 is a frontal, perspective view of a specimen holding device in accordance with the invention.

Referring now to the drawings, in FIG. 1 there is illustrated a specimen holding device 10 having a generally longitudinally extending shape. Originating from the top surface 10' in the device, recesses 11 in the form of dead-end bores of circular cross-section are present which extend perpendicularly to the top surface 10' and serve for reception of the reagent as well as the substance to be analyzed. These recesses 11 are therefore filled by the manufacturer with the reagent in gel form. Since this filling is not particularly simple, depending upon the particular reagent substance, the recesses 11 are interconnected at their lower ends with a filling channel 12 which is illustrated with dashed lines. The filling channel 12 terminates at one end with the opening 12' in one of the outer walls of the specimen holding device. The recesses 11 are all filled uniformly when the device is filled with the gel through this channel. As is further illustrated with dashed lines, this specimen holding device can also be provided on its underside with a row of gear teeth 13, which greatly facilitates transport of the device in an automatic analyzing device. As further illustrated, the specimen carrying device shown here can further comprise on its lateral end surface a dove-tail-formed recess 14 or a dove-tail-formed protusion 15, which permit several specimen holding devices of the same type to be coupled together. This can be of advantage in the case of conducting a series of investigations. In this regard, the coupling links can also be designed in such a manner that the specimen carrying devices are movable with respect to one another while being joined to one another.

Figure 2:
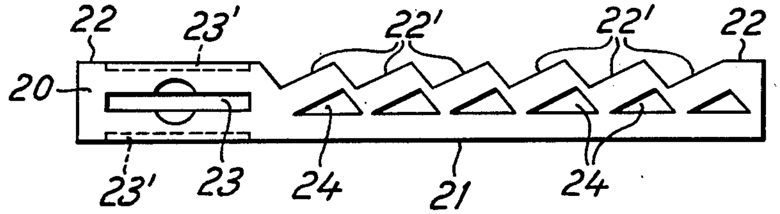
FIG. 2 is a top view of another embodiment of the specimen holding device according to the invention.

FIG. 2 illustrates in top view a further embodiment for the specimen holding device of the invention. As illustrated, this device 20 comprises a planar side surface 21, whereas the side surface 22 opposite thereto is subdivided into a plurality of sections, of which the two most distal sections are parallel to the side surface 21. The intermediate portion of this side surface is subdivided into step-like graduations, each of which is arranged obliquely at the same angle with respect to the longitudinal axis of the device. In its left-hand section, the device 20 includes an elongated, narrow recess 23 for receiving a data-carrying means. In place of the recess 23 there can also be provided an alternative form of recess 23' in one of the side walls of the device (shown in dashed lines). Recesses 24 of triangular cross section are arranged in the obliquely arranged portions 22' of the side surface 22. The design facilitates the photoelectric evaluation of the reagent, by providing that the illumination arrangement takes place perpendicularly to the surface 22', whereas the photoelectric observation takes place perpendicularly to surface 21. In this way it is prevented that light emanating from the illumination arrangement reaches the photoelectric receiving device. Obviously, the recesses could also have other shapes, and in particular, they could be of generally circular cross sectional configuration.

Figure 3:
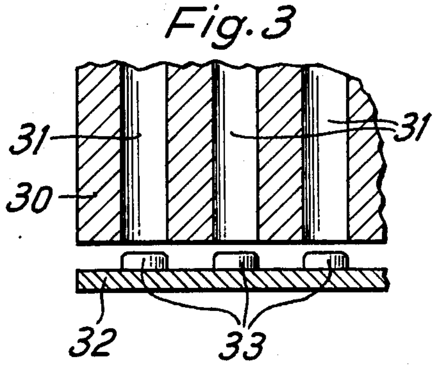
FIG. 3 is a partial cross sectional view of yet another embodiment of the specimen holding device of the invention.

FIG. 3 illustrates in cross-section a portion of another specimen holding device 30 according to the invention, in connection with which the recesses 31 are designed as bores passing completely through the device. In order to close-off these recesses 31, there is provided a carrier 32 which comprises plugs 33 on its upper sides. The plugs correspond in their diameter to the cross-section of the recesses 31. After filling the bores with the reagent, the bores are then closed off by insertion of the carrier 32.

Figure 4:
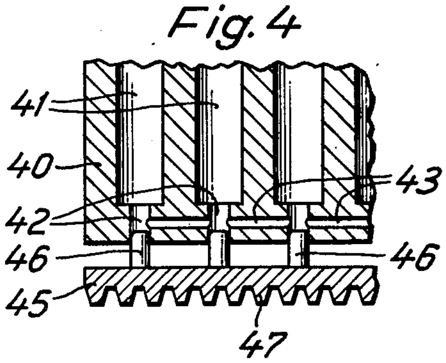
FIG. 4 is a partial cross-sectional view of still another embodiment of the specimen holding device of the invention.

FIG. 4 illustrates an embodiment of the specimen carrying device 40 which is similar to that illustrated in FIG. 3. In this embodiment, the recesses 41 are designed as dead-end bores, which are each connected to the outside by a channel 42. There is also provided a filling channel 43 which interconnects each of the channels 42, and in general as illustrated in FIG. 1 for the channel 12, is directed at one end of the specimen holding device 40. Adapted to the channels 42 is a carrier 45 having corresponding plugs 46, which when press-seated into the channels 42 are introduced to such extent that the channel 43 remains open. After filling the recesses 41 with the reagent, the carrier 45 is completely pressed onto the device 40. In this way, the plugs 46 slide upwardly in the channels 42 and close-off the recesses 41 with respect to one another by closing-off the channel 43. On the lower side of the carrier 45 is included a gear-tooth system 47 which facilitates transport of the specimen holding device.

Figure 5:
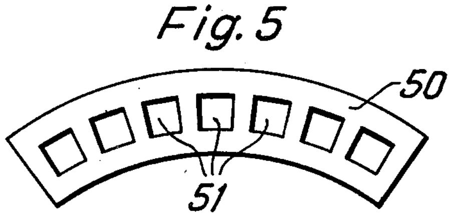
FIG. 5 is a top view of a specimen holding device according to the invention in the shape of an arcuate section.

FIG. 5 illustrates in top view a specimen holding device 50 which has an arcuate shape. The recesses 51 in this illustrated embodiment have trapezoidal cross-section.

Although particular combinations of details are illustrated in the specific embodiments, it is apparent to a person of ordinary skill in the art that these individual features can also be combined and/or modified to produce other embodiments falling within the scope of the present invention, without departing from the general concept of the invention.

What is claimed is:

1. A device for holding a reagent and a fluid substance to be analyzed upon reaction with the reagent to produce a visual change, comprising:

a. a generally horizontally axially elongated, generally solid block of a transparent material, said block having longitudinal side surfaces, at least one of said side surfaces enabling viewing through the block;

b. plural means for holding both the reagent and the fluid substance to be analyzed, with said fluid substance overlying the upper surface of the reagent before reaction therewith, said holding means including a plurality of elongated recesses extending downwardly from the top surface of the block, said recesses being positioned to permit separate lateral viewing, transverse to said at least one side surface, of each recess and of the reaction taking place therein between the reagent and the fluid substance in a region contiguous to the surface of the reagent, and c. means for closing off the bottom ends of said recesses, said closing-off means including removable plug members adapted for insertion into the bottom ends of the recesses.

2. The device as defined by claim 1, further comprising means including a recess in one surface of said block for receiving identifying indicia in a position which is readable by lateral viewing.

3. The device as defined by claim 1, wherein said solid piece is a generally rectangular block and wherein said recesses are arranged with their longitudinal axis perpendicular to the top surface of said block.

4. The device as defined by claim 1, wherein said solid block has an arcuate shape.

5. The device as defined by claim 1, wherein said recesses are of generally circular cross-section and wherein said device further comprises means comprising a hollow conduit extending axially within said solid block for interconnecting the lower ends of said recesses, said conduit terminating on one surface of said solid block.

6. The device as defined by claim 5, wherein said conduit terminates on only one side surface of said solid block.

7. The device as defined in claim 1, further comprising means including a hollow conduit extending axially within said solid block for interconnecting the lower ends of said recesses when said plug members are at least partially withdrawn from said recesses, said conduit terminating on one surface of said solid block.

8. The device as defined by claim 7, wherein said closing means comprises means for transporting said device along the longitudinal axis thereof, said transporting means including a gear-tooth system extending longitudinally along said close-off means.

9. The device as defined by claim 1, further comprising means positioned on one of the outer surfaces of said device for transporting said device along the longitudinal axis thereof.

10. The device as defined by claim 9, wherein said transport means comprises a gear-tooth system extending longitudinally along said device.

11. The device as defined by claim 1, further comprising means attached to at least one outer surface of said solid block for coupling one of said devices to another like device.

12. The device as defined by claim 11, wherein said coupling means includes a dove-tail member.

13. The device as defined by claim 1, further comprising a gelled chemical reagent contained in said recesses.

14. The device as defined by claim 1, wherein said closing off means comprise means for opening and closing off all of said recesses simultaneously.

15. A device for holding a reagent and a fluid substance to be analyzed upon reaction with the reagent to produce a visual change, comprising:

a. a generally horizontally axially elongated, generally solid block of a transparent material, said block having longitudinal side surfaces, at least one of said side surfaces enabling viewing through the block;

b. plural means for holding both the reagent and the fluid substance to be analyzed, with said fluid, substance overlying the upper surface of the reagent before reaction therewith, said holding means including a plurality of elongated recesses extending downwardly from the top surface of the block, said recesses being positioned to permit separate lateral viewing, transverse to said at least one side surface, of each recess and of the reaction taking place therein between the reagent and the fluid substance in a region contiguous to the surface of the reagent, and c. means for closing off the bottom ends of said recesses, wherein said recesses comprise at least one planar side-wall surface which forms an angle different from 90° with the longitudinal axis of said solid block, whereby light entering perpendicularly to said planar side-wall surface does not emanate along the line of transverse viewing.

16. A device for holding a reagent and a fluid substance to be analyzed upon reaction with the reagent to produce a visual change, comprising:

a. a generally horizontally axially elongated, generally solid block of a transparent material, said block having longitudinal side surfaces, at least one of said side surfaces enabling viewing through the block;

b. plural means for holding both the reagent and the fluid substance to be analyzed, with said fluid substance overlying the upper surface of the reagent before reaction therewith, said holding means including a plurality of elongated recesses extending downwardly from the top surface of the block, said recesses being positioned to permit separate lateral viewing, transverse to said at least one side surface, of each recess and of the reaction taking place therein between the reagent and the fluid substance in a region contiguous to the surface of the reagent, and c. means for closing off the bottom ends of said recesses, wherein one of the longitudinal side surfaces of said solid block is sub-divided into a plurality of segments corresponding to the number of said recesses, each segment having a wall surface arranged at a common acute angle with respect to the longitudinal axis of said solid body, whereby light entering perpendicularly to said segment wall surface does not emanate along a line of transverse viewing.

17. The device as defined by claim 16, wherein each of said recesses comprises at least one planar side-wall surface which is oriented parallel to said segment wall surface.

18. A method for analyzing a fluid substance comprising the steps of placing in each of the elongated recesses of a device comprising:

a. a generally horizontally axially elongated, generally solid block of a transparent material, said block having longitudinal side surfaces, at least one of said surfaces enabling viewing through the block;

b. plural means for holding both the reagent and the fluid substance to be analyzed, with said fluid substance overlying the upper surface of the reagent before reaction therewith, said holding means including a plurality of elongated recesses extending downwardly from the top surface of the block, said recesses being positioned to permit separate lateral viewing, transverse to said at least one side surface, of each recess and of the reaction taking place therein between the reagent and the fluid substance in a region contiguous to the surface of the reagent, and c. means for closing off the bottom ends of said recesses; a reagent which is reactive with said substance to produce a detectable indication function, adding said fluid substance to each recess so that the fluid substance overlies the upper surface of the reagent, whereby a detectable indication function is produced in said recesses, and observing said indication function by lateral viewing through each of said recesses.

19. The method of claim 18, wherein said recesses are of generally circular cross-section and wherein said device further comprises means comprising a hollow conduit extending axially within said solid block for interconnecting the lower ends of said recesses, said conduit terminating on one surface of said solid block and wherein said step of placing a reagent in said recesses comprises introducing said reagent through said conduit.

20. The method of claim 18, wherein said recesses pass completely through said solid block and said close-off means includes downwardly removable plug members adapted to said recesses, wherein said device further comprises means including a hollow conduit extending axially within said solid block for interconnecting the lower ends of said recesses when said plug members are at least partially withdrawn from said recesses, said conduit terminating on one surface of said solid block and wherein said step of placing a reagent in said recesses comprises introducing said reagent through said conduit and inserting said plug members in the recesses.

21. The method of claim 18, wherein said observing step comprises illumination of each recess from one lateral side of said block and photoelectrically observing said recess from the opposite side of said block.

22. The method of claim 21, wherein said recesses comprise at least one planar side-wall surface which forms an angle different than 90° with the longitudinal axis of said solid block, whereby illuminating light entering perpendicularly to said planar side-wall surface is not photoelectrically observed in the line perpendicular to the longitudinal axis of said block.

23. The method of claim 21, wherein one of the longitudinal side surfaces of said solid block is sub-divided into a plurality of segments corresponding to the number of said recesses, each segment having a wall surface arranged at a common acute angle with respect to the longitudinal axis of said solid body, whereby illuminating light entering perpendicularly to said planar side-wall surface is not photoelectrically observed in the line perpendicular to the longitudinal axis of said block.

24. The method of claim 21, wherein said device further comprises means positioned on one of the outer surfaces of said device for transporing said device along the longitudinal axis thereof and wherein said observing step includes the step of automatically transporting said device by said transporting means.

25. The method of claim 24, wherein said device further comprises means attached to at least one outer surface of said solid block for coupling one of said devices to another like device and said transporting step includes transporting a plurality of said devices connected together by said coupling means.

* * * * *